United States Patent [19]

Sugimoto et al.

[11] Patent Number: 4,486,417
[45] Date of Patent: Dec. 4, 1984

[54] FLUROCARBON-WATER EMULSION FOR HYPERALIMENTATION CONTAINING MALTOSE

[75] Inventors: Kaname Sugimoto; Toshio Miyake, both of Okayama, Japan

[73] Assignee: Kabushiki Kaisha Hayashibara Seibutsu Kagaku Kenkyujo, Okayama, Japan

[21] Appl. No.: 320,745

[22] Filed: Nov. 12, 1981

[30] Foreign Application Priority Data

Dec. 2, 1980 [JP] Japan ................................. 55-170766

[51] Int. Cl.³ ...................... A61K 31/70; A01N 57/26
[52] U.S. Cl. .................................... 424/180; 424/199; 424/350
[58] Field of Search ........................ 424/180, 199, 350

[56] References Cited

U.S. PATENT DOCUMENTS

| 3,169,094 | 2/1965 | Wretlind | 424/199 |
|---|---|---|---|
| 3,778,381 | 12/1973 | Posano et al. | 252/311 |
| 4,254,105 | 3/1981 | Fukuda | 424/170 |
| 4,280,996 | 7/1981 | Okamoto | 424/199 |
| 4,397,870 | 8/1983 | Sloviter | 424/325 |

FOREIGN PATENT DOCUMENTS

| 725596 | 1/1966 | Canada . | |
| 785387 | 10/1957 | United Kingdom | 424/180 |
| 1192479 | 5/1970 | United Kingdom . | |
| 1477732 | 6/1977 | United Kingdom | 424/180 |
| 1520754 | 8/1978 | United Kingdom . | |
| 1575958 | 10/1980 | United Kingdom . | |

OTHER PUBLICATIONS

Watanabe et al., Gastroenterol JPN 15(2): 152–159, 1980.
Tanaka, J. Kansai Med. Univ. 27(4): 648–666, 1976.
Sakai, Jutsugo Taisha Kenkyu Kaishi 1976, 10(1), 208–212 (Japan).

Primary Examiner—Sidney Marantz
Assistant Examiner—Shawn P. Foley
Attorney, Agent, or Firm—Browdy and Neimark

[57] ABSTRACT

A process for the production of an O/W emulsion for hyperalimentation comprising homogenization of a composition comprising hydrophobic substance, emulsifier, water and maltose into minute droplets of O/W emulsion. The emulsion can provide a higher caloric nutritive supplement to patients than conventional emulsions using glycerin. It is stable over a wide temperature range and it can be stored for long periods of time. The emulsion is particularly useful in emergency medical situations where enteral or parenteral hyperalimentation is required for the patient.

2 Claims, No Drawings

FLUROCARBON-WATER EMULSION FOR HYPERALIMENTATION CONTAINING MALTOSE

DETAILED DESCRIPTION OF THE INVENTION

The present invention relates to a process for the production of a hitherto unknown oil-in-water emulsion (referred as "O/W emulsion" hereinafter) for hyperalimentation which is advantageously feasible for parenteral hyperalimentation, such as intravenous injection, or enteral hyperalimentation such as oral administration or intubation feeding.

There have been known conventional emulsions for intravenous injection such as oil emulsions (Japan Kokai No. 44,622/76), and fluorocarbon emulsions for medical use (Japan Kokai No. 47,265/74). Since the former can supply intravenously oil having a high nutritive value to patients, its demand is gradually increasing year by year. On the other hand, the latter is an artifical blood, based on the utilization of the oxygen-carrying action of fluorocarbons, which can be injected intravenously to patients on profuse bleeding, and its practical realization is also in great expectation.

Both emulsions are prepared by homogenization of a composition consisting of hydrophobic substance such as oil or fluorocarbon; emulsifier, such as lecithin or oxyethylene-propylene copolymer; water; and glycerin as an isotonic agent.

However, since the minute droplets in the emulsion are unstable, and readily susceptible to destruction and/or aggregation by temperature variation and/or long periods of storage, the production of an emulsion having a higher nutritive value per vial and also that of a dietetically well-balanced emulsion, with the use of sugars, amino acids, vitamins and minerals, met with great difficulties.

The present inventors have investigated processes for the production of an O/W emulsion for hyperalimentation, particularly for intravenous injection, by which sufficient calories can be supplied to patients. These efforts have resulted in the finding that an O/W emulsion, prepared by homogenization of a composition comprising hydrophobic substance such as oil or fluorocarbon, emulsifier, water and maltose, to give minute droplets of O/W emulsion, is suitable as a stable and high-caloric emulsion for hyperalimentation, especially for intravenous injection.

Particularly, after investigation using sugars such as pentose, hexose, aldose, ketose, sugar alcohol, monosaccharide and disaccharide in place of glycerin, which had been used as an isotonic agent in the production of an emulsion for intravenous injection, the inventors reached to an unexpectable finding that maltose in the O/W emulsion exhibits an isotonic action as well as a strong emulsion-stabilizing effect in said emulsion.

Furthermore, since in order to obtain the desirable isotonic point with maltose and about 4-fold higher concentration is required than in the case of glycerin, and maltose is readily utilizable, maltose can supply advantageously an about 4-fold higher calorie content, and therefore is an optimal ingredient for the production of an O/W emulsion which provides a higher nutritive value to patients.

The details of the present invention are explained by the following description.

As to the ingredients composing the emulsion, the use of the ingredients purified to the greatest possible level is desirable because they are directly, for example, intravenously, administered in vivo.

As to the hydrophobic substances usable in the present invention, any hydrophobic substance can be used in the present invention so far as it can be injected into patients without fear of side-effects, and fullfil the present objectives. Preferable hydrophobic substances are oils which are utilizable and taken into the metabolic system, such as cotton-seed oil, corn oil, palm oil and soy bean oil; fluorocarbons which have an oxygen-carrying action; fat-soluble vitamins such as vitamin A, vitamin E, vitamin K and vitamin D; and steroid hormones such as estrogen, progestron and androgen.

As to the emulsifiers usable in the present invention, any emulsifiers can be used so far as they are innocuous, and lead to the formation of minute droplets of O/W emulsion in the presence of the above mentioned hydrophobic substance, water and maltose on mechanical homogenization. Preferable emulsifiers are phospholipids, such as egg lecithin and soy bean lecithin; and nonionic polymers such as oxyethylene-propylene copolymer.

As to the maltose preparations usable in the present invention, the use of a highly-purified, pyrogen-free maltose preparation having a maltose content of about 80% d.s.b. or more is desirable. Since maltose causes no side-effects in vivo, and is readily utilizable therein, it is advantageously usable as a sugar ingredient for intravenous injection, oral administration or intubation feeding.

A preferable formulation of the emulsion is about 1–50 w/w % for hydrophobic substance, about 0.1–10 w/w % for emulsifier, about 1–20 w/w % for maltose, and about 40 w/w % or more for water.

As to the methods by which a composition having the above described formulation is homogenized into minute droplets of O/W emulsion, any method can be employed in the invention so far as the minute droplets can be obtained thereby. For example, a partially homogenized mixture, obtained by vigorous agitation of said composition having the formulation, is further homogenized with a high-pressure homogenizer into minute droplets of O/W emulsion having an average particle size of about 0.5μ, preferably about 0.01–0.3μ. The resultant is sterilized to obtain the O/W emulsion for hyperalimentation, for example, for intravenous injection, after careful filtration by membrane filter and subsequent distribution into vials if necessary.

Since the emulsion is highly stable and can also supply high caloric nutrients, it may be prepared, if necessary, in combination with one or more members selected from the group comprising biologically-active substances, such as antibiotics and hormones, and various nutrients, such as vitamins, amino acids, peptides and minerals, so that a dietetically well-balanced emulsion for hyperalimentation is obtained to realize an integrated nutrient supplement to patients.

In addition to the use in intravenous injection wherein the emulsion can be administered in a small dosage within a brief time, or in a large dosage over long time by instillation injection, since the emulsion which is prepared with oil as the hydrophobic substance to effect the integrated nutrient supplement can be administered through nasal cavity, esophagus, stomach or intestine to patients in operation or in unconsciousness, and the maltose in the emulsion is readily utilizable and taken into the metabolic system, the emulsion is advantageously feasible as a fluid food in intubation feeding as well as in usual administration.

The following experiments explain the present invention in more detail.

EXPERIMENT 1

Affinities of various sugars to hydrophobic substance

A composition, consisting of 5 parts of soy bean oil, 85 parts of water and 10 parts of one of a variety of sugar preparations (special grade), was stirred vigorously with a mechanical mixer, HOMO-MIXER, registered trade mark of TOKUSHUKI KAKO Co. Ltd., Osaka, Japan, for ten minutes to effect partial homogenization. Control preparations are prepared similarly as above except that the sugar was replaced with the same amount of water or completely omitted.

After transferring the emulsions into Nestler's test tubes and standing therein at 25° C. for two days under ambient conditions, observation was made on the phase separation between the upper layer, containing soy bean oil, and the lower layer containing the minute droplets of O/W emulsion. Then, a small portion of the lower layer was collected for a microscopic observation, about 600 magnitudes, determining the average particle size and numbers of the droplets in the emulsion.

The experimental results led to a conclusion that the smaller and more the droplets are, the more turbid the lower layer is.

The experimental results are shown in TABLE 1.

As obvious from the results as shown in TABLE 1, since the phase separation does not occur completely immediately after the homogenization, and the lower layer contains minute droplets of O/W emulsion, the sugar exhibits an affinity in a small degree to the hydrophobic substance, and the affinity is usually reduced by the presence of sugar. However, since, like water and not like other sugars, maltose exhibits a comparable affinity to the hydrophobic substance without reduction of the affinity, the affinity of maltose to the hydrophobic substance, observed, is comparable or higher than that of glycerin which has previously been used as an isotonic agent in the production of an emulsion for intravenous injection.

TABLE 1

| Sugar | Turbidity | Particle size | Particle number | Weighting |
|---|---|---|---|---|
| — (control) | strong | fairly small | extremely large | excellent |
| water (control) | strong | fairly small | extremely large | excellent |
| glycerin | moderate | fairly small | large | good |
| xylitol | moderate | fairly small | moderate | fair |
| sorbitol | moderate | moderate | moderate | fair |
| mannitol | weak | moderate | moderate | poor |
| glucose | slight (semitransparent) | fairly large | small | poor |
| fructose | slight (semitransparent) | fairly large | small | poor |
| galactose | slight (semitransparent) | fairly large | small | poor |
| lactose | slight (semitransparent) | large | small | very poor |
| sucrose | slight (semitransparent) | large | small | very poor |
| maltose (present invention) | strong | small | extremely large | excellent |

EXPERIMENT 2

Emulsion-stabilizing activities of various sugars in an O/W emulsion for hyperalimentation A composition, consisting of 10 parts of soy bean oil, 1.2 parts of egg lecithin as the emulsifier, 85 parts of water and 10 parts of one of a variety of sugar preparations (special grade), was homogenized similarly as in the previous EXPERIMENT to effect partial homogenization. The resultant was further homogenized with a high-pressure homogenizer, equipped with spraying devices, manufactured by Gaulin Corporation, U.S.A. under nitrogen atmosphere and at an elevated pressure of about 650 kg/cm$^2$ into minute droplets of O/W emulsion. Control preparations were prepared similarly as above except that the sugar preparation was replaced with the same amount of water or completely omitted.

After transferring the resultant emulsions into Nestler's test tubes and standing in a 50° C. incubator for one month, observations were made on the phase separation, and aggregation and number of the droplets by an electromicroscopic procedure, 5,000 magnitudes, and the obtained data were compared with those obtained immediately after the homogenization to evaluate the emulsion-stabilizing activities of the sugars.

The experimental results are shown in TABLE 2.

As obvious from the results as shown in TABLE 2, the stability of the minute droplets of O/W emulsion was reduced usually by the presence of sugar. How-

TABLE 2

| Sugar | Phase separation | Particle aggregation (average size, μ) | | Reduction of particle number | Weighting |
|---|---|---|---|---|---|
| — (control) | no occurrence | no occurrence | (0.1) | no occurrence | excellent |
| water (control) | no occurrence | no occurrence | (0.1) | no occurrence | excellent |
| glycerin | no occurrence | slight | (0.3) | slight | good |
| xylitol | slight | slight | (0.5) | slight | fair |
| sorbitol | slight | slight | (0.5) | slight | fair |
| mannitol | slight | slight | (0.8) | slight | fair |
| glucose | moderate | moderate | (1.3) | moderate | poor |
| fructose | moderate | moderate | (1.2) | moderate | poor |
| galactose | moderate | moderate | (1.5) | moderate | poor |
| lactose | distinct | distinct | (5.0) | distinct | very poor |
| sucrose | distinct | distinct | (4.3) | distinct | very poor |
| maltose (present invention) | no occurrence | no occurrence | (0.1) | no occurrence | excellent | ever, since, like water and not like other sugars, maltose exhibits a comparable emulsion-stabilizing activity without reduction of the stability, the emulsion containing maltose is comparable or more superior than that which contains glycerin as the isotonic agent.

Since in view of the property of maltose as an isotonic agent an about 10% isotonic maltose solution is about 4-fold higher in concentration than 2.5% isotonic glycerin solution, and maltose added in the emulsion is readily utilizable, the emulsion can supply a higher calorie content to patients; thus, the production of an O/W emulsion for hyperalimentation which can realize a higher nutritive supplement in hitherto unexpectable level is easily realized thereby.

From the above described advantages, the present emulsion can be advantageously feasible in emergency situations such as operation or profuse bleeding where a high caloric nutrient supplement is urgently required by a small dosage of intravenous injection. Furthermore, the emulsion may be mixed with other emulsions for intravenous injection prior to use so far as the mixing does not result in the phase separation and/or aggregation of the minute droplets.

Several embodiments of the present invention are disclosed hereinafter.

EXAMPLE 1

A composition, consisting of 10 parts of soy bean oil, 1.0 part of soy bean lecithin, 90 parts of water and 10 parts of maltose, was homogenized similarly as in EXPERIMENT 1 into a partially homogenized mixture, and the mixture was then further homogenized with a ultra-sonicator, 20 KHz, 200 W, into minute droplets of O/W emulsion having an average particle size of about $0.2\mu$ or less. Thereafter, the emulsion was filtered carefully with a membrane filter according to conventional methods, and distributed into vials which were then sterilized by heating to obtain the O/W emulsion for intravenous injection.

The emulsion is advantageously feasible for intubation feeding as well as for the above described use.

EXAMPLE 2

A composition, consisting of 10 parts of corn oil, 1.0 part of soy bean lecithin, 5 parts of maltose and 1.2 parts of glycerin, was partially homogenized similarly as in EXPERIMENT 1, and the resultant mixture was further homogenized with a high-pressure homogenizer, equipped with spraying devices, manufactured by Gaulin Corporation, USA, under nitrogen atmosphere and at an elevated pressure of about 600 kg/cm$^2$ into minute droplets of O/W emulsion having an average particle size of about $0.3\mu$ or less. Thereafter, the emulsion was filtered carefully with a membrane filter according to conventional methods, and then distributed into vials which were then sterilized by heating to obtain the O/W emulsion for intravenous injection.

EXAMPLE 3

A composition, consisting of 20 parts of cotton-seed oil, 2.5 parts of egg lecithin, 80 parts of water and 8 parts of maltose, was homogenized similarly as in EXAMPLE 2 into minute droplets of O/W emulsion having an average particle size of about $0.3\mu$ or less. Thereafter, the emulsion was distributed into vials which were then sterilized by heating to obtain the O/W emulsion for intravenous injection.

The emulsion is advantageously feasible as a fluid food for intubation feeding as well as for the above described use.

EXAMPLE 4

A composition, consisting of 5 parts of soy bean oil, 1.5 parts of egg lecithin, 65 parts of water, 5 parts of maltose, 0.01 part of calcium chloride, 0.04 parts of thiamine and 0.04 parts of riboflavin, was homogenized similarly as in EXAMPLE 2 into minute droplets of O/W emulsion having an average particle size of about $0.2\mu$ or less. Thereafter, the emulsion was distributed into vials which were then sterilized by heating to obtain the O/W emulsion for intravenous injection.

The emulsion is advantageously feasible as fluid food for intubation feeding as well as for the above described use.

EXAMPLE 5

A composition, consisting of 25 parts of fluorocarbon (perfluoro decalin), 4 parts of egg lecithin, 85 parts of water and 9 parts of maltose, was homogenized similarly as in EXAMPLE 2 into minute droplets of O/W emulsion having an average particle size of about $0.3\mu$ or less. Thereafter, the emsulion was distributed into vials which were then sterilized by heating to obtain the fluorocarbon emulsion for intravenous injection.

EXAMPLE 6

A composition, consisting of 15 parts of fluorocarbon (perfluoro tributyl amine), 5 parts of oxyethylene-propylene copolymer (average molecular weight about 8,200), 100 parts of water, 5 parts of maltose, 0.06 parts of sodium chloride, 0.03 parts of potassium chloride, 0.02 parts of calcium chloride and 0.031 part of sodium lactate, was homogenized similarly as in EXAMPLE 1 into minute droplets of O/W emulsion having an average particle size of about $0.2\mu$ or less. Thereafter, the emulsion was distributed into vials which were then sterilized by heating to obtain the fluorocarbon emulsion for intravenous injection.

EXAMPLE 7

A composition, consisting of 9 parts of soy bean oil, 1.0 parts of vitamin E acetate, 1.5 parts of soy bean lecithin, 90 parts of water and 10 parts of maltose, was homogenized similarly as in EXAMPLE 2 into minute droplets of O/W emulsion having an average particle size of about $0.3\mu$ or less. Thereafter, the emulsion was distributed into bottles which were then sterilized by heating to obtain the O/W emulsion for hyperalimentation.

The emulsion is advantageously feasible as a fluid food for oral administration or intubation feeding as well as for intravenous injection.

What we claim is:

1. In an intravenously injectable fluorocarbon-water emulsion of the type wherein a pharmaceutically-acceptable fluorocarbon having an oxygen carrying capacity is emulsified in water, the improvement comprising an emulsion of:
   (a) 1–50 w/w % of said fluorocarbon;
   (b) 0.1–10 w/w % of an emulsifier selected from the group consisting of soy bean lecithin, egg lecithin and oxyethylene-propylene copolymer;
   (c) 1–20 w/w % of a pyrogen-free high-purity maltose having a maltose content of 80% d.s.b. or higher; and
   (d) said water ad 100 w/w %;
   said emulsion having an average particle size of $0.1$–$0.3\mu$ in diameter.

2. An emulsion as set forth in claim 1, wherein said fluorocarbon is perfluoro decalin or perfluoro tributyl amine.

* * * * *